United States Patent
Maschke

(10) Patent No.: US 7,457,659 B2
(45) Date of Patent: Nov. 25, 2008

(54) METHOD AND DEVICE FOR EXAMINING THE SKIN

(75) Inventor: Michael Maschke, Lonnerstadt (DE)

(73) Assignee: Siemens Aktiengesellschaft, Munich (DE)

(*) Notice: Subject to any disclaimer, the term of this patent is extended or adjusted under 35 U.S.C. 154(b) by 413 days.

(21) Appl. No.: 11/001,601

(22) Filed: Dec. 1, 2004

(65) Prior Publication Data

US 2005/0119551 A1 Jun. 2, 2005

(30) Foreign Application Priority Data

Dec. 1, 2003 (DE) ................................ 103 56 088

(51) Int. Cl.
*A61B 6/00* (2006.01)
(52) U.S. Cl. ...................... 600/431; 5/601; 600/407; 600/476
(58) Field of Classification Search .............. 600/306, 600/407, 431, 476; 382/108; 5/601
See application file for complete search history.

(56) References Cited

U.S. PATENT DOCUMENTS

| | | | |
|---|---|---|---|
| 4,670,781 A * | 6/1987 | Aubert et al. ................... 348/77 |
| 4,922,909 A * | 5/1990 | Little et al. ................... 600/300 |
| 5,363,854 A * | 11/1994 | Martens et al. .............. 600/477 |
| 5,369,527 A | 11/1994 | McCracken | |
| 5,836,872 A * | 11/1998 | Kenet et al. ................... 600/306 |
| 5,911,126 A * | 6/1999 | Massen ........................ 702/153 |
| 6,208,749 B1 * | 3/2001 | Gutkowicz-Krusin et al. ............................ 382/128 |
| 6,405,072 B1 * | 6/2002 | Cosman ....................... 600/426 |
| 6,427,022 B1 * | 7/2002 | Craine et al. ................. 382/128 |
| 6,571,003 B1 * | 5/2003 | Hillebrand et al. ........... 382/118 |
| 6,761,697 B2 * | 7/2004 | Rubinstenn et al. .......... 600/587 |
| 6,873,340 B2 * | 3/2005 | Luby .......................... 345/619 |
| 6,993,167 B1 * | 1/2006 | Skladnev et al. ............. 382/128 |
| 7,239,906 B1 * | 7/2007 | Green et al. ................. 600/407 |
| 2004/0064974 A1 * | 4/2004 | Schuster ......................... 36/91 |
| 2004/0152976 A1 * | 8/2004 | Hengerer et al. ............. 600/431 |

FOREIGN PATENT DOCUMENTS

| | | |
|---|---|---|
| DE | 196 22 312 A1 | 3/1997 |
| DE | 101 36 192 C1 | 4/2003 |
| EP | 0 667 117 B1 | 8/1995 |
| WO | WO 02/094098 A1 | 11/2002 |
| WO | WO 2094098 A1 * | 11/2002 |

OTHER PUBLICATIONS

Malignes Melanom, "Alarmzelchen der Haut—jetzt rasch zunacharzt", Fortschritee Der Medizin, No. 6, 2003, p. 36.

* cited by examiner

*Primary Examiner*—Ruth S. Smith
*Assistant Examiner*—Jonathan G Cwern

(57) ABSTRACT

For efficient detection or observation of a skin disease, especially skin cancer, methods for examining the skin of a subject and an associated device are specified. Accordingly a camera element is provided, by means of which an image of an area of skin is recorded. The image is fed to an image evaluation unit which uses electronic pattern recognition based on at least one prespecified selection rule to analyze the image for the occurrence of suspect skin marks with, on detection of a suspect skin mark, its location being determined and displayed.

17 Claims, 4 Drawing Sheets

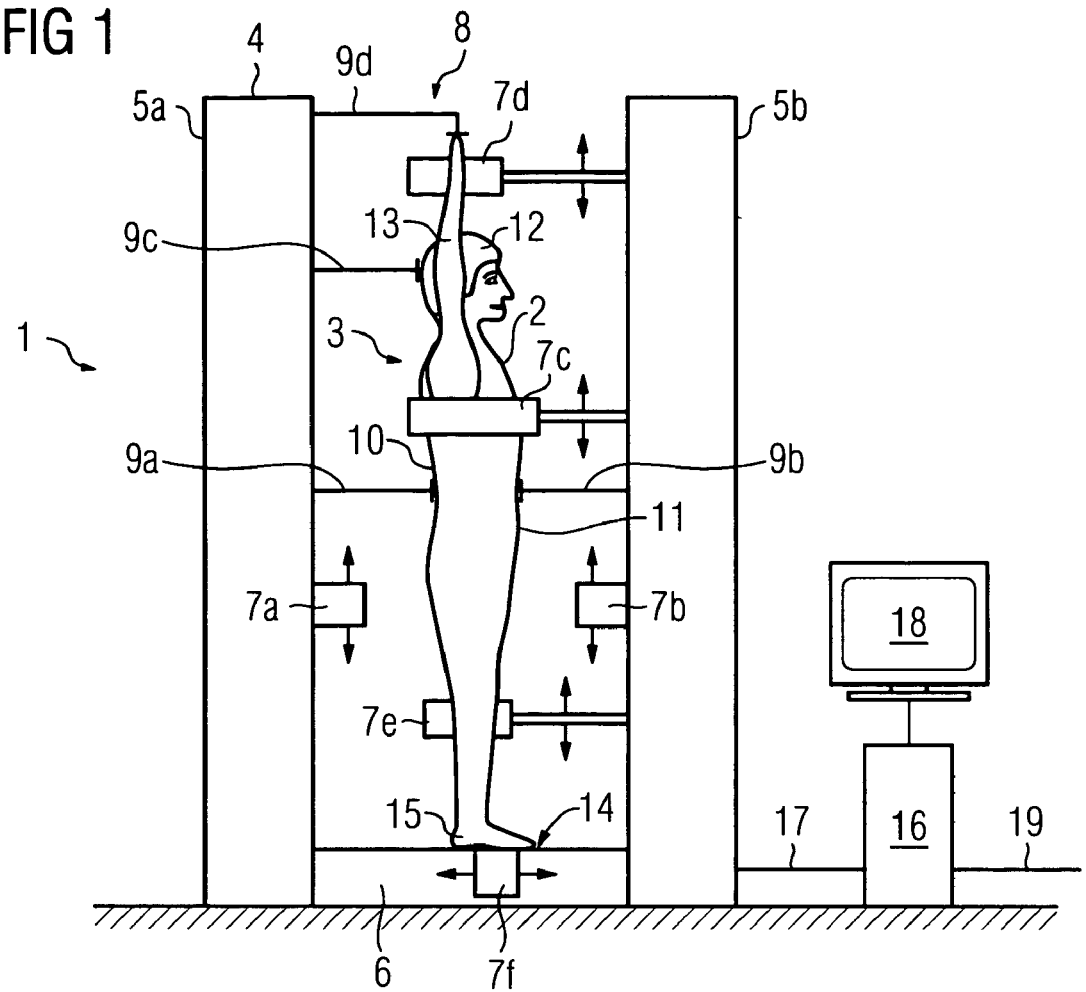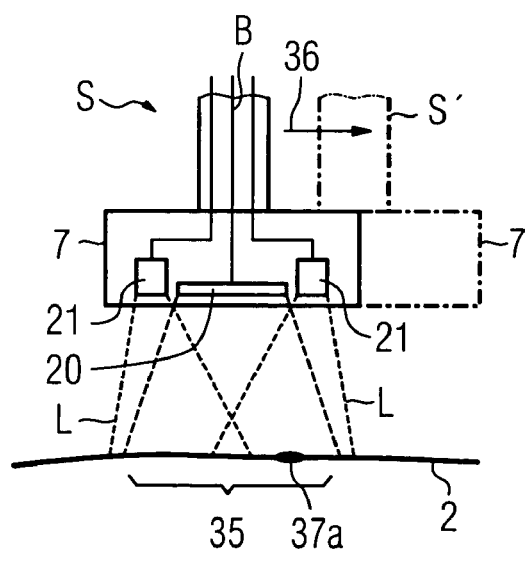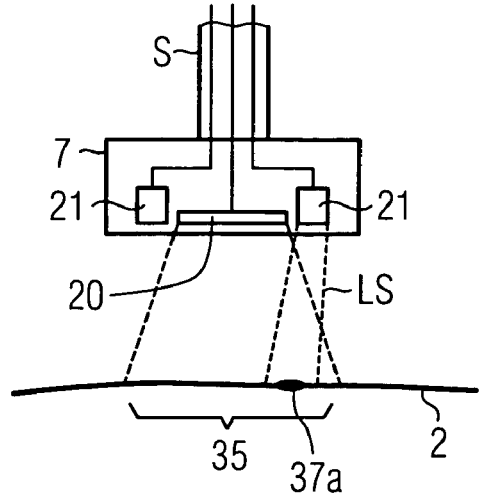

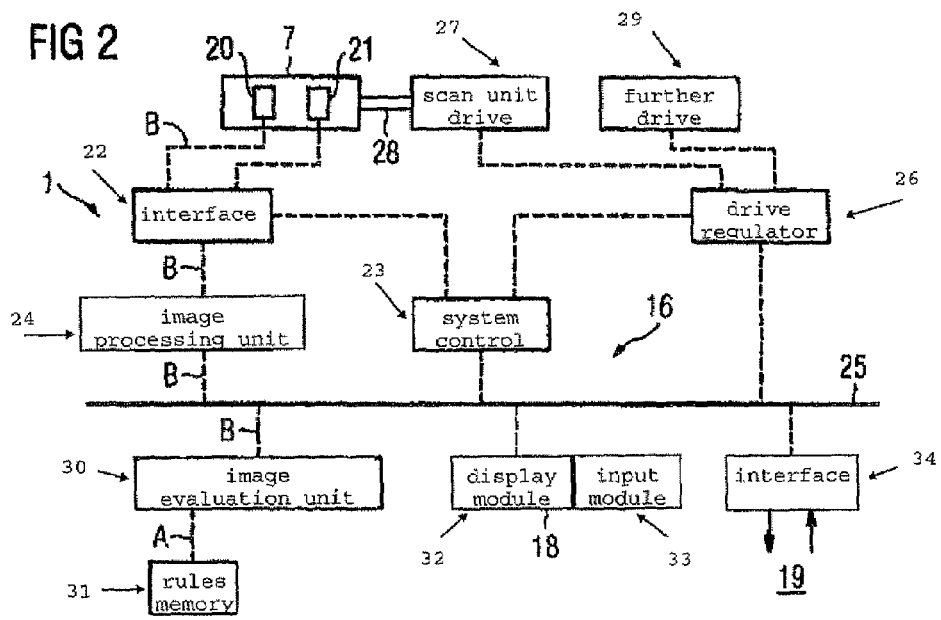
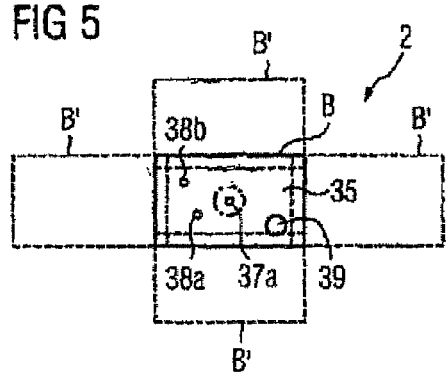
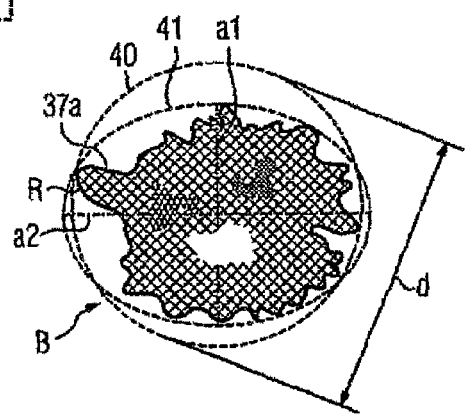

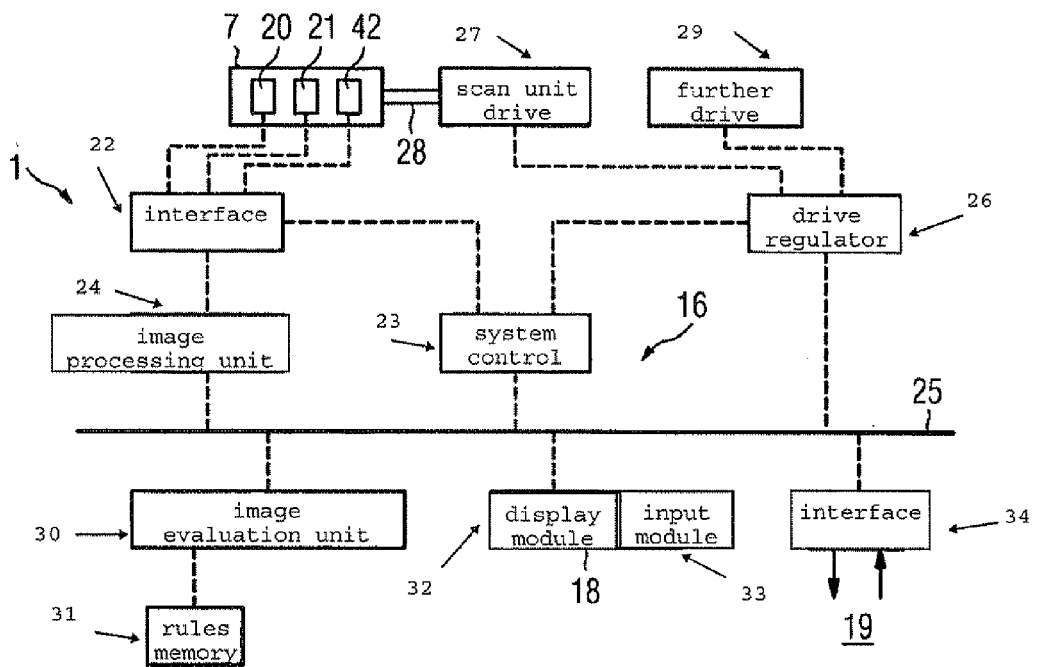
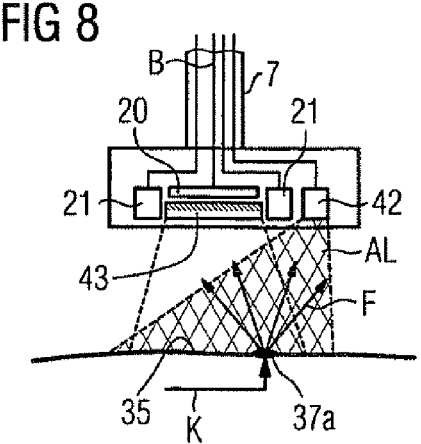

METHOD AND DEVICE FOR EXAMINING THE SKIN

CROSS REFERENCE TO RELATED APPLICATIONS

This application claims priority to the German application 10356088.2 filed Dec. 1, 2003 and which is incorporated by reference herein in its entirety.

FIELD OF INVENTION

The invention relates to a method for examining a subject's skin, especially within the framework of a preventive skin cancer examination or of a skin cancer therapy. The invention further relates to a device for executing the method.

BACKGROUND OF INVENTION

Recently there has been a marked increase in the frequency of incidences of skin cancer. This is caused in particular by the increasing trend towards intensive exposure to sunlight. The most frequent fatal skin disease is what is known as a malignant melanoma, which has an incidence in Central Europe of around 12 cases/100,000 people a year (Fortschritte der Medizin, Nr. 6, 2003—Progress in Medicine No. 6, 2003).

With early diagnosis of the skin disease and immediate initiation of therapy, which as a rule consists of the surgical removal of the diseased tissue, the prospects of recovery are good. The problem however is that of detecting the disease at an early stage.

Previously as a general rule an initial prophylactic examination of the skin was undertaken by a skin specialist. This initial examination is usually undertaken as a visual check using a magnifier. In such cases the skin specialist analyses deviations of the skin, such as pigment flecks. These are normally checked for asymmetry, border, color and diameter. An irregular and non-sharply defined skin deviation with mixed pigmentation and anametically observed growth tendency is a strong suspect for malignancy. Only if such a suspect area of skin is found in the first examination is it generally subjected to a closer analysis using examination methods with greater selectivity (e.g. incident light microscopy).

It is thus of decisive importance, for early detection of skin cancer, that suspect areas of the skin are securely detected in the first examination. This has previously been critical since a malignant melanoma is comparatively inconspicuous at the early stage and the quality of the initial examination thus greatly depends on the thoroughness and duration of the examination with which the skin specialist tracks down the suspect areas of skin. The conventional initial examination must also be undertaken by an experienced doctor and is comparatively time consuming. An efficient early detection of skin cancer is thus problematic and associated with high costs, especially in countries with a large land mass and a comparatively low density of doctors.

An aid designed to enable even unskilled personnel to conduct preliminary examinations for skin cancer is known from U.S. Pat. No. 5,369,527. The aid consists of a transparent, flexible plate, in which, in addition to the magnifier, there are markings made with which the diameter and the asymmetry of a skin mark can be determined.

SUMMARY OF INVENTION

The object of the present invention is to specify a method for examination of the skin which makes possible an especially efficient early detection of skin diseases, particularly of skin cancer. A further object of the invention is to specify a device especially suited to executing the method.

As regards the method, the object in accordance with the invention is achieved by the features of the Claims. As regards the associated device, the object in accordance with the invention is achieved by the features of the Claims.

Accordingly, a camera element is provided as part of the device executing the method, with which an image is recorded of an area of skin of a subject to be examined. The image is fed to an image evaluation unit and is investigated there by means of electronic pattern detection for the incidence of skin marks. Each skin mark found is classified in accordance with prespecified selection rules as suspect, e.g. potentially diseased, or harmless. If a suspect skin mark is detected by the image evaluation unit, its location on the subject's skin is determined. This location is displayed by suitable means so that, if need be, a further more in-depth examination of the skin mark can be conducted.

A significant advantage of the method in accordance with the invention lies in the fact that the initial examination for the presence of a skin disease, especially skin cancer, is automated as far as possible. This leads to a drastic reduction in the time required to conduct the examination. Furthermore the risk of not detecting a diseased skin mark as a result of a careless mistake or lack of experience is excluded. The initial examination does not therefore require the presence of a doctor. Instead it can be undertaken by medical support staff. In particular this allows effective and comparatively low-cost skin cancer prevention, which can also advantageously be used especially in regions with a large land mass as well as a low density of doctors.

For especially effective early detection of diseased areas of the skin there is provision for large parts, especially the entire skin of a subject, to be scanned. For this the camera element is mounted so that it can be moved relative to the subject's skin. The formulation here is to be seen as a relative specification, which thus also includes embodiments in which the camera element is arranged in relation to a spatially fixed system of coordinates, and the subject is moved in relation to the laboratory coordinate system, and thereby in relation to the camera element. Equally a number of movable an/or fixed camera elements can be provided which each cover different regions of the skin surface. As part of conducting the procedure images of different parts of the skin are recorded in different camera positions which together produce an overall picture of the subject's skin.

For the purposes of effective analysis the image of an area of the skin is first examined for the presence of skin marks (or skin flecks). A skin mark here is recognized as being a contiguous area of skin which differs significantly as regards its pigmentation from the rest of the skin. Subsequently geometrical and color characteristics of the skin mark are determined. By checking these characteristics on the basis of one or more specified selection rules the skin mark is classified as suspect or harmless. The skin mark is classified as suspect especially if its diameter, its asymmetry, the variation of its pigmentation and/or the irregularity of its border exceeds a prespecified reference value in each case.

Preferably each of the four selection rules given above is checked, with the skin mark examined being classified as suspect if any of the selection rules are fulfilled. If required, a different method can be used in which only individual selection rules or a subset of the selection rules given above, where necessary in combination with further selection rules not explicitly stated here, are used for checking. Furthermore it would be conceivable for a skin mark to only be classified as suspect where necessary if a number of selection rules are fulfilled simultaneously in a given combination.

If a skin mark is classified as suspect, it is useful to display the image of the area of skin involved, on a screen for example. In addition it also makes sense to directly indicate the location of the skin mark on the subject's skin. For this a light source is advantageously provided in an embodiment of the invention, by means of which a light beam can be projected onto the location of the suspect skin mark. The light source is usefully a component of a scan unit also containing the camera element which can be moved across the subject's skin.

To avoid a misinterpretation of an image because of shadowing etc. the area of skin for which the image is to be recorded is preferably evenly illuminated while the image is being recorded. To this end a light source is also assigned to the camera element. To simplify the device it is advantageous to use this same light source simultaneously for illuminating the skin area during the image recording and for indicating suspect skin marks.

A general problem of any skin examination is that of unequivocally finding again a mark on a subject's skin once it has been identified as suspect, such as the location of a skin mark relative to a spatially fixed laboratory coordinate system, which is naturally subject to a degree of constant movement with the movement of the subject. This problem arises to an increased extent with an automated examination method, in which it is not possible to refer back to the memory capability of a human being who has conducted an examination.

To ensure that the skin mark is found again, an embodiment of the present invention is thus especially advantageous, in which a positioning device is provided in which the body of the subject, and thereby each area of skin, is fixed in a specified examination position. This positioning device usefully includes supports or grips which come into contact with the subject's body at specific points. The positioning device can however alternatively or additionally include color or light markings on which the subject places their hands or feet, or such like.

In addition or alternatively there is provision, as a further means of matching the location of the image of an area of skin to the actual area of skin, for at least one significant skin structure to be determined as a position marking. Any bodily characteristics which are visible on the surface of the body can serve as a skin structure, for example nose, mouth, eyes, nails, elbow, belly button, nipples as well as the detected skin marks themselves. Determining the skin structures means that an unmistakable "map" of the subject's skin, typical of an individual, is created on the basis of which a location on the skin, once determined, can be automatically found again at any point, even if, between the first image being taken and the system being reactivated the subject has moved the area of skin involved. The recording of skin structures as position markings is preferably also included in order to place images of adjacent areas of skin correctly next to one another. It is sensible here for such images of adjacent areas of skin to overlap in an edge area.

Whereas the basic type of the invention given above is based on a photographic image of the skin, in a further development of the invention the optical effect of the skin is explicitly changed by administration of a fluorescent contrast medium. The use of such a contrast medium for detecting a tumor is known per se and is described in DE 101 09 539 A1 for example. The effect of such an examination method is based on the contrast medium being increasingly enhanced because of the accelerated change of material in the tumorous tissue. If the affected tissue is now illuminated with a suitable excitation light, after the contrast medium has been administered, the contrast medium added to the tumor radiates fluorescent light. The tumorous tissue thus stands out from the healthy tissue by its luminance. A further device advantageously developed to utilize the fluorescence effect comprises an excitation light source which is implemented in particular by a laser light diode. To increase the sensitivity of the method in relation to the radiated fluorescent light a filter sensitive to fluorescent light is preferably placed in front of the camera element here.

In order to work with different contrast mediums as required, a number of different excitation light sources and fluorescent filters relative to the radiated or transmitted light can be selected. This choice is preferably made automatically. The operating personnel in this case merely have to enter the name of the contrast medium used or—even more simply— read it in using a bar code etc.

In a further development of the inventive idea the application of the method is not restricted to a one-off examination. Instead there is provision in the invention, using multiple skin examinations offset in time based on changes in identified skin characteristics, to separate benign skin characteristics from malignant ones and to observe the development of a melanoma already identified, during the course of therapy for example. To this end an image of an area of skin recorded at an earlier stage is held as a reference image. This reference image is compared with a current image, i.e. an image of the same area of skin taken later. If a number of images of different areas of skin are recorded, the system refers back to a corresponding reference image for each current image. In this case the skin marks identified within the area of skin are examined with regard to how they have changed over time. Skin marks which have changed significantly over time are again displayed on the screen and if necessary that area of the subject's body is displayed.

The image is advantageously compared with the associated reference image by generating a difference image in which the change between the two images is highlighted.

Since two images of a subject's skin recorded at different times will in every likelihood not depict precisely the same area of skin because the subject has moved in relation to the recording device, it makes sense, to increase the accuracy of the difference image, to initially adjust the current image and the reference image in relation to one another. This adjustment is preferably made by moving the images so that skin structures and or skin marks which can be identified both in the current image and also in the reference image as position markings overlay each other. The difference image is then created from the images adjusted to each other in this way.

BRIEF DESCRIPTION OF THE DRAWINGS

Exemplary embodiments of the invention are explained in more detail below on the basis of a drawing. These show:

FIG. 1 a schematic view from above of a device for examining the skin of a subject with a number of scan units which can be moved over the subject's skin, FIG. 2 a schematic block diagram of the device according to FIG. 1

FIG. 3 a schematic cross section of a scan unit of the device according to FIG. 1 during recording of an image of the area of skin of the subject, FIG. 4 in a diagram in accordance with FIG. 3, the scan unit showing a display of a skin mark classified as suspect, FIG. 5 a schematic diagram of the image of an area of skin recorded by the device in accordance with FIG. 1, FIG. 6 an enlarged detail view according to FIG. 5 of the image of a suspect skin mark, FIG. 7 in a diagram in accordance with FIG. 2, an alternative version of the device, FIG. 8 in a diagram in accordance with FIG. 3, a scan unit of the device in accordance with FIG. 7 during recording of an image of the skin during illumination of the skin area with a fluorescence-generating excitation light, FIG. 9 in a diagram in accordance with FIG. 2, a further embodiment of the device, and FIG. 10 a schematic diagram of the creation of a difference image of an area of the skin by overlaying a current image with a reference image taken at an earlier point in time.

DETAILED DESCRIPTION OF INVENTION

Figure 9:
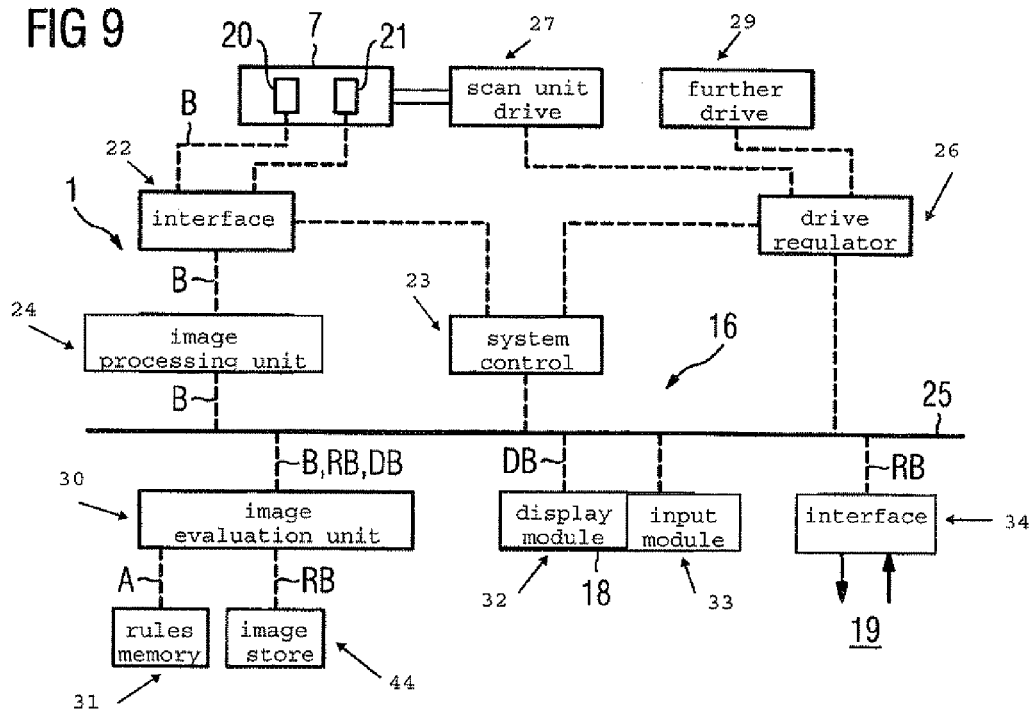

Parts and variables which correspond to each other are always shown by the same reference symbols in all the Figures.

The device 1 shown in FIG. 1 for examining the skin 2 of a subject 3 comprises a stand 4. The stand 4 comprises two side walls 5a and 5b (depending on the embodiment, side panels etc. as well, ) as well as a base plate 6, arranged between the side walls 5a, 5b. The facing sides of the side walls 5a and 5b, as well as the base plate 6, carry a number of scan units 7, identified individually by 7a to 7f, for photographic imaging of the skin 2. The side walls 5a, 5b also carry a positioning unit 8, which fixes the subject 3 between the side walls 5a and 5b in a prespecified examination position. The positioning unit 8 includes supports 9a to 9c which are in contact with the subject in their back 10, stomach 11 or head 12 area. Two further supports 9d (of which only one can be seen in the diagram in FIG. 1) are embodied as grips which are located above the head of the subject 3 and which the subject 3 holds onto by extending their arms 13. The positioning device 8 further includes a marking 14 made on the base plate 6 on which the subject 3 places their feet 15 to position themselves for the examination.

Each side wall 5a and 5b carries a scan unit 7a or 7b, which can be moved from the head to the foot of the subject 3 so that by means of the scan unit 7a the skin 2 on the back of the subject 3 and with the scan unit 7b the skin 2 on the front of the subject 3 can be recorded. Two further scan units 7c are used to record the skin on the subject's sides, which start from side wall 5b and move to the left or right of the subject 3, and of which again only one is visible in FIG. 1. Further scan units 7d, 7e and 7f are used to record the skin on the outside of the subject's arms, their shoulders and the side areas of their head (adjacent to the head 12) or the insides of the legs or the soles of the feet. This means that the scan units 7a to 7f enable the entire skin surface of the subject 3 to be scanned.

The device 1 further includes a control unit 16 (especially one embodied as a computer) which is connected to the stand via a data line 17 and is equipped with an input/output unit 18 (including a screen, a keyboard and a mouse for example). The control unit 16 is further connected to an external data transmission network 19, especially the Internet.

The internal structure of the device 1 is shown in FIG. 2 in a schematic block diagram. It can be seen from this diagram, as it can from FIGS. 3 and 4, that each scan unit 7 contains a camera element 20 as well as one or more light sources 21, especially implemented by light-emitting diodes. The camera element 20, which in particular is embodied as a CCD panel, and the light sources 21 are connected via an interface 22 to the control unit 16. The interface 22 activates the camera element 20 and the light sources 21 and receives in the form of image data the images B created by the camera element 20. The interface 22 is itself activated by a system control 23 which is embodied as a software module of the control unit 16. The interface 22 is further connected for output of the images B with an image preprocessing unit 24 which serves to edit the images transferred over the interface 22, especially for equalizing signaling and brightness, as well as for image processing and image buffering in real time. The image processing unit is in turn connected to a data bus 25 of the control unit 16.

The system control 23 further activates a drive regulator 26. The drive regulator 26 in its turn controls a drive 27 for moving the scan unit 7. The drive 27 acts on the scan unit 7 via a mechanical coupling 28 shown schematically.

The drive regulator 26 controls a further drive 29 by means of which the supports 9a through 9d can be adjusted automatically.

The device 1 also has an image evaluation unit 30, in which the images B prepared by the image preprocessing unit 24 are analyzed. The image evaluation unit 30 operates here within the framework of an electronic pattern recognition as defined by a number of selection rules A, which are prespecified to the image evaluation unit 30 by a rules memory 31.

The input/output unit 18 includes, as can be seen from FIG. 2, a display module 32, especially a screen, and also at least one input module 33, especially a keyboard, a mouse, etc. The control unit 16 communicates with the data transmission network 19 via a corresponding interface 34.

The execution sequence of the method is described in more detail in FIG. 3 and FIG. 4. These show a scan unit 7, which contains the camera element 20 as well as the two light sources 21 positioned over the skin 2 of the subject 3 in a first position S. By means of the light sources 21, which provide light source light L, an area 35 of the skin 2 opposite the scan unit 7, in the field of view of the camera element 20 is illuminated, preferably with white light. The digital image B of the area of skin 35 is now taken by means of the camera element 20 and directed to the interface 22 (FIG. 2) and examined in the control unit 16 in a way described in greater detail below for the occurrence of suspect skin marks.

The scan unit 7 is then moved in the direction of arrow 36 into a subsequent position S' in which an image B' (FIG. 5) of an adjacent area of skin is recorded. In this way the entire skin 2 is exposed photographically by means of the scan units 7a to 7f.

If a skin mark, as shown schematically in FIG. 3 and FIG. 4. and indicated by the reference symbol 37a is found within the area of skin 35 and classified by the image evaluation unit 30 as suspect, its location on the skin 2 is determined. The scan unit 7 is moved back after the scan process to the assigned position S in the area of skin 35 and the suspect skin mark 37a is displayed visually by a beam of light LS generated by one or more light sources 21 projected onto the skin 2. At the same time an enlarged image of the skin mark 37a can be shown on the display module 32 if necessary. It is however also possible just as easily to transmit the image of the skin mark 37a via the data transmission network 19 to any given remote location. This allows a precise remote diagnosis of skin cancer and is thus of particular benefit in regions with a large land mass and a comparatively low density of experienced specialists.

FIG. 5 and FIG. 6 show simplified schematic diagrams of the principle of the image evaluation undertaken by the image evaluation unit 30. FIG. 5 shows image B of the area of skin 35 as well as, indicated by dashed lines, four images B' of adjacent areas of skin. As can be seen from FIG. 5, the images B and B' are recorded such that their edges overlap. This enables a pattern comparison to be used to allow an unequivocal spatial arrangement of the skin areas of adjacent images B, B' to be established, so that a skin mark can also be unequivocally detected if it extends over a number of adjacent images B, B'. If necessary a complete image of the skin 2 of the subject 3 can be created by combining adjacent (individual) images B, B'.

As part of the process of identification of diseased points on the skin the detection of skin marks 37a and 38a, 38b is initially necessary. The detected skin marks 37a, 38a, 38b are then classified into "suspect", i.e. potentially harmful skin marks 37a and "harmless" skin marks 38a, 38b.

The detection of the skin marks 37a and 38a, 38b as such is undertaken by examining the pigmentation, i.e. the skin coloring. In this case any contiguous skin surface is recognized as a skin mark 37a, 38a, 38b of which the pigmentation deviates significantly, i.e. by more than a prespecified tolerance range, from the basic color of the skin 2. The basic color of the skin 2 can for example be determined by forming the average of the color value of all pixels of the image B (or B'). Preferably rules are specified to the image evaluation unit 30 by means of which skin marks 37a, 38a, 38b can be distinguished from other significant skin structures such as mouth, nose, eyes, fingernails, belly button, nipples, etc., which can also be distinguished from the basic color of the skin 2 in image B through their color shadowing. This discrimination between skin marks 37a, 38a, 38b on the one hand and skin structures 39 is preferably undertaken by pattern comparison with typical stored patterns of typical skin structures. A local preference is again preferably specified for the skin structures 39 stored as patterns. In other words the image evaluation unit 30 "knows" that there is more likely to be an occurrence of a specific skin structure 39 in the environment of a specific area of the skin 35. If for example the skin area 35 shown in FIG. 5 is the lower part of the stomach 1 of the subject 3, there is high likelihood that the image evaluation unit 30 will assign the skin structure 39 to the belly button of the subject 3 and will validate this basic assumption on the basis of the pattern comparison. Preferably the location of skin marks 37a, 38a, 38b and skin structures 39 as position marking together with the images B and B' A "map" so to speak of the skin 2 of the subject 3 is thus created. This "map" enables the device 1 to find again an area of skin 35 once scanned if the subject 3 has moved away from their original examination position.

The skin marks 37a and 38a, 38b are classified using a closer inspection of the form and pigmentation of each skin mark 37a and 38a, 38b. This is done by determining the diameter d and the asymmetry a of the skin marks 37a, 38a, 38b as well as the irregularity of their border R and the variation v of their pigmentation.

To illustrate a possible execution of this method the skin mark 37a is shown enlarged in FIG. 6. It can be seen from the illustration that the diameter d is definable as the diameter of the circle 40, into which the skin mark 37a is precisely mathematically entered.

The variables a, u and v are not shown directly in the diagram for illustrative reasons. A suitable definition for the asymmetry is however produced by the formula $a=a2/a1$. In this formula a1 stands for the short axis and a2 for the long axis of the ellipse 41 into which the skin mark 37a has just been entered. Expediently the ellipse 41 is to be turned in relation to the skin mark 37a so that the quotient a2/a1 is at its maximum.

The irregularity u is to be defined in a suitable way, e.g. as the length of the border R, standardized to the length of the border of the ellipse 41. The amount of the irregularity u in this case becomes greater, the more the form of the skin mark 37a deviates from the regular elliptical form.

The variation v of the pigmentation can be determined for example by the standard deviation of the color values of all pixels of the image B associated with the skin mark 37a.

The definitions given above provide a simple option for determining the geometrical and color characteristics of the skin mark 37a in an automated method. As an alternative however a plurality of further relationships for definition of the variables d, a, u and v or of similar variables for characterizing the geometry and color of skin marks are conceivable.

To classify the skin mark 37a into "suspect" or "harmless" the variables d, a, u, v are compared using the prespecified selection rules A with associated limit values in each case. Thus skin mark 37a is classified as suspect if its diameter d exceeds a prespecified reference value, if its asymmetry a exceeds a prespecified reference value, if the irregularity u of the border R exceeds a prespecified reference value and/or if the variation v of the pigmentation exceeds a prespecified reference value.

Whereas the device depicted in FIG. 2 performs a simple automated visual check of the skin 2 of the subject 3, with a further development of the device 1 embodied in FIG. 7 the fluorescence effect of a contrast medium K (FIG. 8) can be employed for improved detection of a tumorous skin mark 37a. In the embodiment in accordance with FIG. 7 the scan unit 7 of the device 1 includes an additional excitation light source 42 compared to the variant shown in FIG. 2, said light source being especially embodied as a laser diode. The camera element 20 of the scan unit 7 further has a light filter 43 (FIG. 8) placed in front of it which is effectively transparent for fluorescent light F of a specified wavelength.

As schematically indicated in FIG. 8, in the course of a further development of the method the contrast medium K is administered to the subject 3 before the image is recorded. This can be done by injection, administering by mouth or by application to the skin 2. The contrast medium K accepted into the body of the subject 3 accumulates as a result of increased material change in tumorous tissue. In other words the concentration of the accepted contrast medium K in the area of the harmful skin mark 37a is greater than in the remaining skin area 35. While the image B is being recorded the skin area 35 is now illuminated by the excitation light source 42 with excitation light AL of a specific wavelength. The wavelength of the excitation light AL is dimensioned in this case such that through the excitation light AL the contrast medium K is excited to radiate fluorescent light F. In this way the tumorous skin mark 37a stands out from the rest of the area of skin 35 as a bright surface. This enables skin mark 37a to be distinguished from radial skin marks 38a, 38b.

The light filter 43 largely masks out the background light. Tumorous tissue is thus made particularly easy to see on the image.

To enable the development of a skin disease over time to be investigated, or even to enable the skin disease to be detected from the development of the skin marks over time, a development of the device 1 shown in FIG. 9 features an image store 44 in which one or more reference images RB of the skin 2 of the subject 3 taken at an earlier time are stored. The image store 44 can be any temporary or permanent memory medium, e.g. a hard disk, CD-Rom, DVD or similar. As an alternative to local storage of the reference image RB in the image store 44 the reference image RB can also be obtained from an external data source via the data transmission network 19.

In the embodiment of the device 1 shown in FIG. 9 the image evaluation unit 30 is embodied to compare a current image of an area of skin 35 with of a reference image RB of essentially the same area of skin 35 and to filter out changes between image B and reference image RB with regard to the skin marks 37a and 38a, 38b contained therein. The image evaluation unit 30 performs this process by creating a difference image DB of the image B and associated reference image RB.

Figure 10:
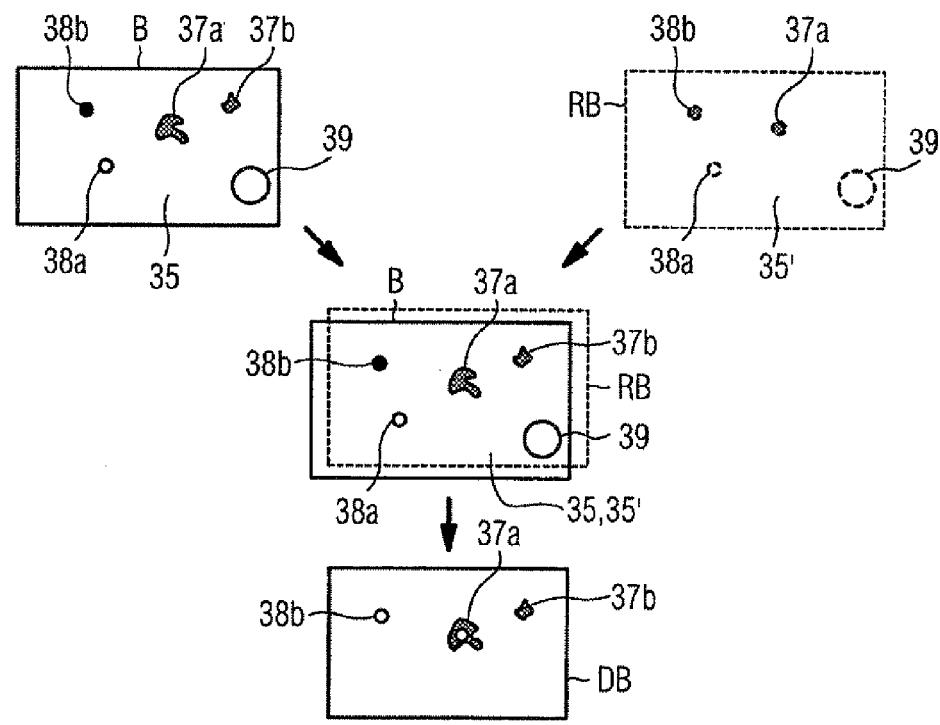

This process is shown in more detail in FIG. 10. The current image B and the reference image RB (indicated by a dashed outline) of essentially the same area of skin 35 or 35' form the starting point. The reference image RB contains the skin mark 37a classified as suspect, the skin marks 38a and 38b classified as harmless as well as the skin structure 39. The current image B recorded later additionally contains a further skin mark 37b classified as suspect. The skin mark 37a has grown markedly compared to the reference image RB. The skin marks 38a and 38b are unchanged as regards their size. However with skin mark 38b a difference in the pigmentation can be established on comparison of the images B and RB.

To create the difference image DB the image B and the reference image RB are initially shifted in relation to each other such that the relevant skin marks 37a, 38a, 38b and skin structures 39 of both images B and RB overlay each other as well as possible. The difference image DB is formed from the images B, RB adjusted in this way.

The difference image DB now contains the change over time in the state of the skin of the subject 3. In particular the growth of skin mark 37a of the changed color surrounding skin mark 38b documented by the difference image DB can give rise to a new assessment of a skin mark which in the first examination was still classified as harmless. If necessary, regardless of the actual size of the skin mark, its rate of growth can be selected as an additional selection rule for classifying a skin mark as "suspect".

With the further development of the method and the device 1 according to FIGS. 9 and 10 a refined detection and examination to accompany therapy of a skin cancer is thus possible.

The features of the different embodiments of the device 1 according to FIGS. 2, 7 and 9 can be combined in any given way. Likewise, within the framework of the present invention, numerous variations not shown here in detail are conceivable. For example the device 1 could be equipped with a different number of scan units 7 from that depicted in FIG. 1, especially a single scan unit 7. This scan unit 7 could for example be accommodated on a C-arm which is movable around the axis of subject 3. Furthermore the subject 3 in could be positioned lying down or standing up on a turntable.

Preferably the device 1 is designed for the use of different contrast media K. In this case there is provision for enabling the wavelength of the excitation light AL to be selected to match the relevant contrast medium K. Likewise a number of light filters 43 are provided here 43, which are placed in front of the camera element 20 depending on the contrast medium K selected. Preferably the relevant contrast medium K is adapted automatically by entering the designation of the contrast medium K via a keyboard or reading it in via a bar code reader.

The invention claimed is:

1. A method for examining skin of a living human, comprising:
providing a scan unit stand including two side walls, a positioning unit which is carried on the side walls and which fixes the human between the side walls in a pre-specified examination position, and a base plate on which the human places his/her feet to position themselves for examination, the base plate attached to the side walls, the positioning unit further including automatically adjustable supports which are positioned for contacting the human's back, stomach, or head area;
recording an image of an area of the skin by at least one recording element movably located on the scan unit stand;
illuminating evenly the area of the skin by a light source while the image is being recorded, wherein the light source is movably located on the scan unit stand;
providing the image to an image evaluation unit;
analyzing the image via the image evaluation unit for a suspect skin mark;
using an electronic pattern recognition which is based on a pre-specified selection rule to identify the suspect skin mark;
determining a location of the suspect skin mark by the image evaluation unit; and
indicating the location of the suspect skin mark by a beam of light projected onto the skin by the light source,
automatically adjusting the supports via a drive regulator which concurrently controls movement of the at least one movable recording element to provide coordinated movement between the human and the at least one movable recording element as an aid in arranging the human in the appropriate pre-specified position.

2. The method as claimed in claim 1, further comprising displaying the location of the suspect skin mark.

3. The method as claimed in claim 2, further comprising:
identifying the location of the skin mark or a significant skin structure; and storing the location identified as a position marking.

4. The method as claimed in claim 1, wherein recording the image is performed by a recording element which is a camera.

5. The method as claimed in claim 1, further comprising:
moving the recording element over the skin; and recording the images of different areas of the skin, the skin being scanned in the manner of a scanning process.

6. The method as claimed in claim 1, further comprising:
recognizing a skin mark as a contiguous area of the skin which differs in pigmentation from a remaining area of the skin.

7. The method as claimed in claim 6, wherein the skin mark is classified as the suspect skin mark if the skin mark has a diameter exceeding a pre-specified reference value.

8. The method as claimed in claim 6, wherein the skin mark is classified as the suspect skin mark if an asymmetry of the skin mark exceeds a pre-specified reference value.

9. The method as claimed in claim 6, wherein the skin mark is classified as the suspect skin mark if a variation of the pigmentation of the skin mark exceeds a pre-specified reference value.

10. The method as claimed in claim 6, wherein the skin mark is classified as the suspect skin mark if an irregularity of a border of the skin mark exceeds a pre-specified reference value.

11. The method as claimed in claim 1, further comprising:
administering a contrast medium to the human before the image is recorded, the contrast medium for accumulating in a tumorous skin tissue; and
illuminating the area of the skin during the image recording with an excitation light for exciting the contrast medium to radiate a fluorescent light.

12. The method as claimed in claim 11, further including providing the excitation light from a laser light.

13. The method as claimed in claim 11, wherein a light filter sensitive to a wavelength of the fluorescent light is placed in front of the recording element for recording the image.

14. The method as claimed in claim 13, further comprising:
comparing a current image of the area of the skin with a previous image of approximately the same area of the skin; and
creating a difference image of the current image and the previous image by filtering out the changes between the current image and the previous image.

15. The method as claimed in claim 13, further comprising:
comparing a current image of the area of the skin with a previous image of approximately the same area of the skin; and
wherein the current image and the previous image of an area of the skin are adjusted on the basis of at least one significant skin structure used as a position marking or common skin mark.

16. The method as claimed in claim 1, further comprising:
comparing a current image of the area of the skin with a previous image of approximately the same area of the skin; and
analyzing and displaying a change over time of the skin mark.

17. A method for examining skin of a living human, comprising:
providing a scan unit stand including two side walls, a positioning unit which is carried on the side walls and which fixes the human between the side walls in a pre-specified examination position, and a base plate on which the human places his/her feet to position themselves for examination, the base plate attached to the side walls, the positioning unit further including automatically adjustable supports which are positioned for contacting the human's back, stomach, or head area; and
recording an image of an area of the skin by at least one movable recording element located on the scan unit stand;
providing the image to an image evaluation unit;
analyzing the image via the image evaluation unit for a suspect skin mark;
using an electronic pattern recognition which is based on a pre-specified selection rule to identify the suspect skin mark;
determining a location of the suspect skin mark by the image evaluation unit; and
further comprising holding the human in a pre-specified position via the positioning unit during the recording of the image,
automatically adjusting the supports via a drive regulator which concurrently controls movement of the at least one movable recording element to provide coordinated movement between the human and the at least one movable recording element as an aid in arranging the human in the appropriate pre-specified position.

* * * * *